US007575903B2

(12) United States Patent
Buchanan et al.

(10) Patent No.: US 7,575,903 B2
(45) Date of Patent: Aug. 18, 2009

(54) CHR AND POMC EFFECTS ON ANIMAL GROWTH

(75) Inventors: Fiona Buchanan, Saskatoon (CA); Tracey D. Thue, Saskatoon (CA); Dianne Winkelman-Sim, Rosetown (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 11/790,511

(22) Filed: Apr. 26, 2007

(65) Prior Publication Data

US 2008/0070252 A1 Mar. 20, 2008

Related U.S. Application Data

(62) Division of application No. 10/814,760, filed on Mar. 31, 2004, now Pat. No. 7,226,743.

(51) Int. Cl.
*C12P 19/34* (2006.01)
(52) U.S. Cl. ..................................................... 435/91.2
(58) Field of Classification Search ........................ None
See application file for complete search history.

(56) References Cited

OTHER PUBLICATIONS

Nakanishi et al. Nature 278 (5703), 423-427 (1979).*
Nakanishi et al. Nature 287 (5784), 752-755 (1980).*
Nakanishi et al. Eur. J. Biochem. 115 (3), 429-438 (1981).*
Screen shot showing online publication on Mar. 21, 2003 ofr Thue and Buchanan Animal Genetics vol. 34 p. 149-150.*
Buchanan et al. Animal Genetics: vol. 36 (2) Apr. 2005p 127-131.*
Bagley C.P., et al. "Growth and Sexual Characteristics of Sucking Beef Calves as Influenced by Age at Castration and Growth Implants," J. Anim. Sci. 67: 1258-1264 (1989).
Barendse W., et al., "A Medium Density Genetic Linkage Map of The Bovine Genome," Mammalian Genome 8: 21-28 (1997).
Buchanan F.C., et al. "Two QTLs for Growth Map to Bovine Chromosome 14," 27th International Conference on Animal Genetics, Minneapolis, Minnesota (Jul. 22-26, 2000).
Buchanan F.C., et al., "Association of A Missense Mutation in The Bovine Leptin Gene with Carcass Fat Content and Leptin mRNA levels," Genet. Sci. Evol. 34: 105-116 (2002).
Buchanan F.C., et al., "A Corticotrophin-Releasing Hormone Polymorphism Associated With Post-Natal Growth in Beef Cattle," Proceedings of the 7th World Congress on Genetics Applied to Livestock Production, CD-ROM communication No. 11-32 (2002 Paper).
Dunn A.J., et al., "Physiological and Behavioral Responses to Corticotropin-Releasing Factor Administration: Is CRF a Mediator of Anxiety or Stress Responses?" Brain Research Reviews 15: 71-100 (1990).
Grobet L., et al., "Molecular Definition of An Allelic Series of Mutations Disrupting the Myostatin Function and Causing Double-Muscling in Cattle," Mammalian Genome 9: 210-213 (1998).
Houseknecht K.L., et al. "The Biology of Leptin: A Review," J. Anim. Sci. 76: 1405-1420 (1998).
Kress D. D., et al., "Beef Sire Expected Progeny Differences Calculated By Three Methods," J. Anim. Sci. 44: 195-202 (1977).
Liu H-X, et al., "Exonic Splicing Enhancer Motif Recognized by Human SC35 Under Splicing Conditions," Molecular and Cellular Biology 20: 1063-1071 (2000).
Liu X-H, et al., "A Mechanism For Exon Skipping Caused By Nonsense or Missense Mutations In BRCA1 and Other Genes," Nat Genet. 27: 55-58 (2001).
Marsh D.J., et al., "Response of Melanocortin-4 Receptor-Deficient Mice to Anorectic and Orexigenic Peptides," Nat. Genet 21: 119-122 (1999).
Pritchard L.E., et al., Pro-Optiomelancortin Processing in The Hypothalamus: Impact on Melanocortin Signaling and Obesity, J. Endocrinol. 172: 411-421 (2002).
Roche P.J., et al., "Nucleotide Sequence of The Gene Coding for Ovine Corticotropin-Releasing Factor and Regulation of Its mRNA Levels by Glucocorticoids," Gene 71: 421-431 (1988).
Schmutz S.M., et al., "Development of the Canadian Beef Reference Herd for Gene Mapping Studies," Theriogenology 55: 963-972 (2001).
SAS, SAS/STAT User's Guide (Release 8.02), SAS Inst. Inc., Cary, NC (1998).
Schumann F.J., et al., "Prophylactic Tilmicosin Medication of Feedlot Calves At Arrival," Can. Vet. J. 31: 285-288 (1990).
Sharpe P.M., et al., "Glucocorticoid Status in Growth, in: Buttery P.J. Haynes N.B., Lindsay D.B. (Eds.)," Control and Manipulation of Animal Growth, Butterworths, London: 207-222 (1986).
Shibahara S., et al., "Isolation and Sequence Analysis of The Human Corticotropin-Releasing Factor Precursor Gene," EMBO J. 2: 775-779 (1983).
Szabo G., et al., "A Deletion in The Myostatis Gene Causes The Compact (Cmpt) Hypermuscular Mutation In Mice," Mammalian Genome 9: 671-672 (1998).
Thue T.D., et al., "A SNP in The Cattle MC4R Gene is Used to Map MC4R to BTA 24," Anim. Genet. 32: 390-391 (2001).
Thue T.D., et al., "Linkage Mapping of POMC to Bovine Chromosome 11," Anim. Genet. 34: 149 (2003).

* cited by examiner

*Primary Examiner*—Teresa E Strzelecka
*Assistant Examiner*—Suchira Pande
(74) *Attorney, Agent, or Firm*—Heenan Blaikie LLP

(57) ABSTRACT

The present invention provides for selection of bovine animals that will display phenotypes associated with increased rates of growth. These phenotypes include hot carcass weight, average daily gain, shipping weight, end of test rib eye area, and adjusted weaning weight which is a measure of post-natal growth, based on the knowledge of their CRH, POMC and MC4R genotypes. The predictive value comes from the discovery that certain single nucleotide polymorphisms (SNPs) in these genes are linked to higher growth rate phenotypes. Specifically, the phenotypes that correlated with specific SNP's are end-of-test rib-eye area, adjusted weaning weight, average daily gain, shipping weight and hot carcass weight. The invention also provides novel kits that can be used in making the determination of these genotypes. The invention further provides for methods of screening *bovines* to predict which animals will have higher growth rate, allowing producers to selectively breed and manage animals based on desired characteristics, thereby maximizing productivity and profitability in commercial meat production operations.

9 Claims, 3 Drawing Sheets

```
                                    4
CGCCCGCTAAA  ▓▓▓▓▓▓▓▓▓▓▓▓▓▓▓▓▓▓▓▓▓▓▓▓▓▓▓▓▓▓▓▓▓▓  11

▓▓▓▓▓▓▓▓▓▓▓▓▓▓▓▓▓▓▓▓▓▓▓▓▓▓▓▓▓▓▓▓▓▓▓▓▓▓▓  Leu  25
                                          CTC

Leu Ser Arg Gly Pro Ile Pro Gly Ala Arg Gln Ala Ser Gln  39
CTC AGC CGG GGG CCC ATC CCG GGT GCC CGG CAG GCA TCA CAG
                    45
His Pro Gln Pro Leu Ser Phe Phe Gln Pro Pro Gln Pro      53
CAC CCC CAG CCC CTG AGT TTC TTC CAG CCG CCG CCG CAG CCC

Gln Glu Pro Gln Ala Leu Pro Thr Leu Leu Arg Val Gly Glu  67
CAG GAA CCC CAG GCT CTG CCC ACC CTA CTC CGT GTT GGG GAG
                                    77
Glu Tyr Phe Leu Arg Leu Gly Asn Leu Asp Glu Thr Arg Ala  81
GAA TAC TTC CTC CGC CTG GGT AAC CTC GAT GAG ACC CGG GCT

Ala Pro Leu Ser Pro Ala Ala Ser Pro Leu Ala Ser Arg Ser  95
GCT CCS CTC TCT CCC GCC GCC TCG CCT CTC GCC AGC AGA AGC

Ser Ser Arg Leu Ser Pro Asp Lys Val Ala Ala Asn Phe Phe  109
AGC AGT CGC CTT TCT CCG GAC AAG GTG GCC GCC AAC TTT TTC

Arg Ala Leu Leu Gln Pro Arg Arg Pro Phe Asp Ser Pro Ala  123
CGA GCG CTG CTG CAG CCC CGG CGC CCA TTC GAC AGC CCA GCG

Gly Pro Ala Glu Arg Gly Thr Glu Asn Ala Leu Gly Ser Arg  137
GGT CCC GCG GAA CGC GGC ACG GAG AAC GCC CTC GGC AGC CGC

Gln Glu Ala Pro Ala Ala Arg Lys Arg Arg ▓▓▓▓▓▓▓▓▓▓▓▓▓▓  151
CAG GAG GCG CCG GCC GCC AGG AAG AGG CGA

▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓  165

▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓  179

▓▓▓▓▓▓▓▓▓▓▓▓▓▓▓▓▓▓▓▓▓▓▓▓▓▓▓▓  Gly Lys ***           190
                              GGG AAA TGA
```

CHR AND POMC EFFECTS ON ANIMAL GROWTH

This application is a divisional patent application of U.S. Ser. No. 10/814,760 filed on Mar. 31, 2004 now U.S. Pat. No. 7,226,743.

The present invention relates generally to methods of selective breeding and management of livestock animals based on particular allelic polymorphisms, and particularly to predicting the growth characteristics of livestock animals based on these allelic polymorphisms.

BACKGROUND OF THE INVENTION

Increased growth rates are typically associated with higher economic returns to beef producers. Consequently, methods to improve growth rate in cattle are of significant benefit to producers. Prior art methods of increasing growth has included such approaches as the use of hormone implants (Bagley et al., 1989), sub-therapeutic levels of antibiotics (Schumann et al., 1990) and by selective breeding based on expected progeny differences (EPD) (Kress et al., 1977). However, hormone implants and the use of antibiotics are becoming unpopular and may be banned in North America in the near future. Therefore, alternative methods of improving growth rates of cattle that don't require artificial forms of stimulation will become increasingly important and desirable in the industry.

Corticotropin releasing hormone (CRH) indirectly causes the release of glucocorticoids (Dunn and Berridge, 1990), naturally occurring hormones that are suggested to be growth inhibitors (Sharpe et al., 1986). Although commonly referred to as a "stress-related hormone", CRH is released from the hypothalamus, an area of the brain known to be involved in appetite control. The release of CRH regulates appetite via two distinct mechanisms: (1) indirectly triggering the release of pro-opiomelanocortin (POMC), and (2) by increasing the production of leptin (FIG. 1)

The up-regulation of POMC levels leads to increased synthesis of alpha melanocyte stimulating hormone (αMSH) which, when bound to the melanocortin-4 receptor, reduces appetite (Marsh et al., 1999). The increase of leptin, which is induced by glucocorticoids, reduces appetite by four other interactions (FIG. 1). Primarily leptin acts to decrease the levels of neuropeptide Y, an appetite stimulant. Leptin also acts to increase POMC levels, an agonist for the melanocortin 4-receptor (MC4R); decrease the levels of antagonist agouti related protein (AGRP); and increase the production of CRH (Houseknecht et al., 1998; Marsh et al., 1999; Pritchard et al., 2002).

The CRH gene comprises two exons, however only exon 2 is translated and codes for the pre-pro-protein (Roche et al., 1988; Shibihara et al., 1983). The CRH gene has been mapped to chromosome 14 (Barendse et al., 1997), and the results of quantitative trait linkage (QTL) mapping suggested an association between a locus for post-natal growth identified on chromosome 14 and the CRH gene (Buchanan et al., 2000). In addition, we previously reported a non-conserved amino acid substitution at position 77 (CRH77) in the pro-peptide region of CRH and showed an association with post-natal growth in beef cattle (Buchanan et al., 2002b).

The POMC pro-hormone peptide is an integral component of the appetite regulation pathway (FIG. 1) and has also been identified by QTL analysis in our unpublished studies as a positional candidate gene for average daily gain and carcass weight. We identified a single nucleotide polymorphism (SNP) in the POMC gene that is translationally silent and used the SNP to map the POMC gene to chromosome 11 in beef cattle (Thue et al., 2003), confirming its position to previously identified QTL loci. We also identified SNPs in two other genes integral to this pathway, leptin and MC4R (Buchanan et al., 2002a; Thue et al., 2001).

We have recently identified a novel SNP in the CRH gene, at position 4 of the signal sequence, equivalent to position 22 of the sequence defined in SEQ ID NO: 1. Together with the existing gene tests for POMC, MC4R and LEP (Buchanan et al., 2002a; Buchanan et al., 2002b; Thue et al., 2001; Thue et al., 2003) we genotyped a group of 256 steers. Our results show that knowledge of genotypes of cattle, with respect to these particular genes, can be used to better predict growth and yield during beef production.

SUMMARY OF THE INVENTION

It is well known to those skilled in the art that single nucleotide polymorphisms (SNPs) can provide a useful way in which to distinguish different alleles of a gene. Furthermore, when the presence of a SNP can be associated with a specific phenotype, the SNP operates as a powerful marker and can be used to predict phenotypic outcomes based on an animal's genotypic makeup. The present invention relates to methods of managing livestock animals, such as cattle and pigs, and taking advantage of genetic factors that affect an animal's appetite. By identifying animals with a particular genotype, with respect to herein described SNP alleles, it is possible to identify animals that will display phenotypes associated with increased growth rate, as compared to animals lacking the desired genotype.

In particular, the present invention relates to methods for establishing the genetically determined predispositions of individual livestock animals, such as cattle and pigs, within a group of such animals, to meet particular desired characteristics with respect to growth, based on the association of specific CRH, POMC or MC4R alleles with an increased appetite and hence growth phenotype.

The present invention provides a method for analyzing the genotype of animals with respect to the CRH, POMC and MC4R genes, and using the genotype information to select animals with desired traits related to animal growth. Such knowledge further permits producers to charge a premium for the more desirable faster-growing phenotype, and permits breeders to selectively breed animals for genotypes that will result in the most desirable phenotypes.

It is therefore an object of the present invention to provide a method for selecting for animals homozygous for the "G" allele at the CRH gene locus, in the knowledge that animals that are "GG" homozygotes will display the desired phenotypes of increased hot carcass weight, increased end of test rib eye area, and increased adjusted weaning weight.

It is a further object of the present invention to provide a method for selecting for animals homozygous for the "T" allele at the POMC gene locus, in the knowledge that animals that are "TT" homozygotes will display the desired phenotypes of increased average daily gain, shipping weight and hot carcass weight.

It is still another object of the present invention to provide a method for selecting for animals having at least one "C" allele at the MC4R gene locus, in the knowledge that animals that are "CG" or "CC" at the MC4R gene locus will display the desired phenotype of increase hot carcass weight.

It is a further object of the present invention to select for animals homozygous for the "G" allele at CRH and the "T" allele at POMC loci, in the knowledge that those animals that are "GG-TT" homozygotes will display concurrent increases in rib-eye area, shipping weight, hot carcass weight and average daily gain.

It is a further object of the present invention that where the desired phenotype is only increased hot carcass weight, that a more efficient method of testing animals is provided, wherein an animal is first tested to determine it's MC4R genotype in the knowledge that an animal with at least on "C" allele at MC4R will display the desired phenotype of increased carcass weight, regardless of the animal's CRH genotype, such that only those animals that are "GG" at MC4R will need to be tested with respect to their CRH genotype in order to determine whether they will display the desired phenotype of increased hot carcass weights.

It is a further object of the present invention to provide a diagnostic kit to be used in the determination of an animal's CRH, POMC and MC4R genotype.

These and other objects, features, and advantages of the invention become further apparent in the following detailed description of the invention when taken in conjunction with the accompanying drawings which illustrate, by way of example, the principles of this invention.

Thus, the invention provides a genetic testing method for the determination of an animal's CRH, POMC and MC4R genotype based on analysis of the presence or absence of specific SNP's, and the use of the knowledge of an animal's genotype such that animals of like genotype can be identified and selected according to the desired phenotypes of increased shipping weight, hot carcass weight, average daily gain and rib-eye area.

DESCRIPTION OF THE FIGURES

While the invention is claimed in the concluding portions hereof, preferred embodiments are provided in the accompanying detailed description which may be best understood in conjunction with the accompanying diagrams where like parts in each of the several diagrams are labeled with like numbers, and where:

FIG. 2: Sequence of the CRH SNP with respect to the nucleotide and protein coding sequences. The SNP of the invention occurs at position 22 of the nucleotide sequence as defined by SEQ ID NO: 1, which corresponds to codon 4 of the protein coding sequence.

DETAILED DESCRIPTION OF THE INVENTION

Figure 1:
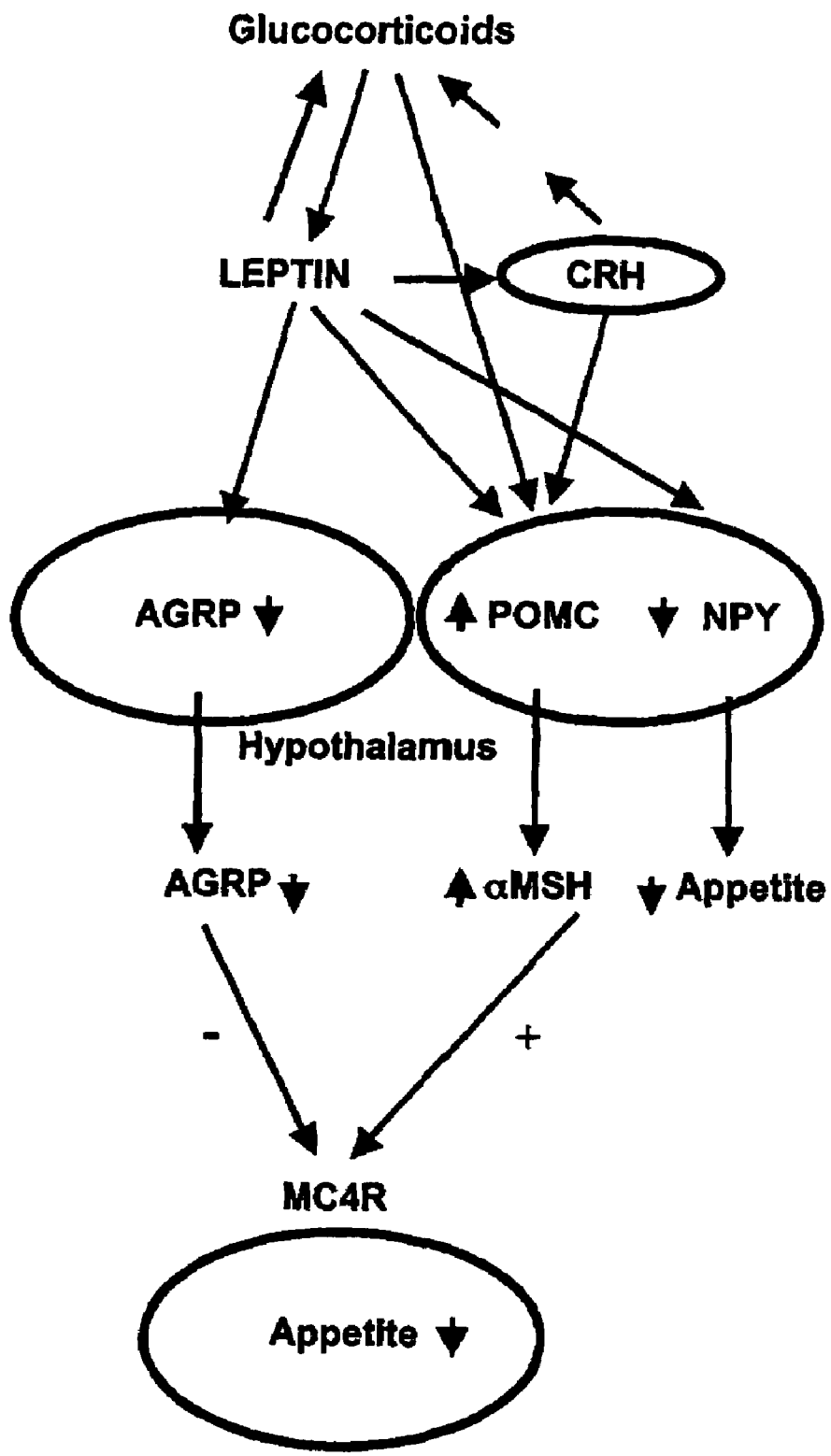
FIG. 1: Appetite pathway. Arrows show the effect of leptins and CRH on neuropeptides that control appetite. Ovals represent neurons in the hypothalamus. CRH—corticotrophin-releasing hormone, AGRP—agouti related protein, POMC—pro-opiomelanocortin, NPY—neuropeptide Y, αMSH—alpha melanocyte stimulating hormone and MC4R—melanocortin 4 receptor.

Definitions:

In the description that follows, a number of terms used in recombinant DNA technology are extensively utilized. In order to provide a clear and consistent understanding of the specification and claims, including the scope to be given such terms, the following definitions are provided:

By "amplifying a segment" as used herein, is meant the production of sufficient multiple copies of the segment to permit relatively facile manipulation of the segment.

Manipulation refers to both physical and chemical manipulation, that is, the ability to move bulk quantities of the segment around and to conduct chemical reactions with the segment that result in detectable products.

A "segment" of a polynucleotide refers to an oligonucleotide that is a partial sequence of entire nucleotide sequence of the polynucleotide.

A "modified segment" refers to a segment in which one or more natural nucleotides have been replaced with one or more modified nucleotides. A "modified, labeled segment" refers to a modified segment that also contains a nucleotide, which is different from the modified nucleotide or nucleotides therein, and which is detectably labeled.

An "amplification primer" is an oligonucleotide that is capable of annealing adjacent to a target sequence and serving as an initiation point for DNA synthesis when placed under conditions in which synthesis of a primer extension product which is complementary to a nucleic acid strand is initiated.

By "analysis" is meant either detection of variations in the nucleotide sequence among two or more related polynucleotides or, in the alternative, determining the full nucleotide sequence of a polynucleotide. By "analyzing" the hybridized fragments for an incorporated detectable label identifying the suspected polymorphism is meant that, at some stage of the sequence of events that leads to hybridized fragments, a label is incorporated. The label may be incorporated at virtually any stage of the sequence of events including the amplification, cleavage or hybridization procedures. The label may further be introduced into the sequence of events after cleavage and before or after hybridization. The label so incorporated is then observed visually or by instrumental means. The presence of the label identifies the polymorphism due to the fact that the fragments obtained during cleavage are specific to the modified nucleotide(s) used in the amplification and at least one of the modified nucleotide is selected so as to replace a nucleotide involved in the polymorphism.

The term "animal" is used herein to include all vertebrate animals, including humans. It also includes an individual animal in all stages of development, including embryonic and fetal stages. As used herein, the term "production animals" is used interchangeably with "livestock animals" and refers generally to animals raised primarily for food. For example, such animals include, but are not limited to, cattle (*bovine*), sheep (*ovine*), pigs (*porcine* or *swine*), poultry (*avian*), and the like. As used herein, the term "cow" or "cattle" is used generally to refer to an animal of *bovine* origin of any age. Interchangeable terms include "bovine", "calf", "steer", "bull", "heifer" and the like. As used herein, the term "pig" or is used generally to refer to an animal of *porcine* origin of any age. Interchangeable terms include "piglet", "sow" and the like.

The term "antisense" is intended to refer to polynucleotide molecules complementary to a portion of an RNA marker of a gene, as defined herein. "Complementary" polynucleotides are those that are capable of base pairing according to the standard Watson-Crick complementarity rules, where purines base pair with pyrimidines to form combinations of guanine paired with cytosine (G:C) and adenine paired with either thymine (A:T) in the case of DNA, or adenine paired with uracil (A:U) in the case of RNA. Inclusion of less common bases like inosine, 5-methylcytosine, 6-methyladenine, hypoxanthine and others in hybridizing sequences does not interfere with pairing.

By the term "complementarity" or "complementary" is meant, for the purposes of the specification or claims, a sufficient number in the oligonucleotide of complementary base pairs in its sequence to interact specifically (hybridize) with the target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

By the term "composition" is meant, for the purposes of the specification or claims, a combination of elements which may include one or more of the following: the reaction buffer for the respective method of enzymatic amplification, plus one or more oligonucleotides specific for CRH, POMC or MC4R gene polymorphisms, wherein said oligonucleotide is labeled with a detectable moiety.

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time. The products of such a reaction are commonly referred to as amplification products.

"Denaturation" of a template molecule refers to the unfolding or other alteration of the structure of a template so as to make the template accessible for duplication or hybridization. In the case of DNA, "denaturation" refers to the separation of the two complementary strands of the double helix, thereby creating two complementary, single stranded template molecules. "Denaturation" can be accomplished in any of a variety of ways well known to those skilled in the art, including heat or by treatment of the DNA with a base or other chemical denaturant.

A "detectable amount of product" refers to an amount of amplified nucleic acid that can be detected using standard laboratory tools. A "detectable marker" refers to a nucleotide analog that allows detection using visual or other means. For example, fluorescently labeled nucleotides can be incorporated into a nucleic acid during one or more steps of a cyclic polymerase-mediated reaction, thereby allowing the detection of the product of the reaction using, e.g. fluorescence microscopy or other fluorescence-detection instrumentation.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated when the oligonucleotide is hybridized to amplified gene polymorphism sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent or fluorescent molecules. Various fluorescent molecules are known in the art that are suitable for use to label a nucleic acid substrate for the method of the present invention. The protocol for such incorporation may vary depending upon the fluorescent molecule used. Such protocols are known in the art for the respective fluorescent molecule.

By "detectably labeled" is meant that a fragment or an oligonucleotide contains a nucleotide that is radioactive, that is substituted with a fluorophore or some other molecular species that elicits a physical or chemical response can be observed by the naked eye or by means of instrumentation such as, without limitation, scintillation counters, colorimeters, UV spectrophotometers and the like. As used herein, a "label" or "tag" refers to a molecule that, when appended by, for example, without limitation, covalent bonding or hybridization, to another molecule, for example, also without limitation, a polynucleotide or polynucleotide fragment, provides or enhances a means of detecting the other molecule. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence, electrochemiluminescence, ramanspectroscopy, calorimetric, hybridization protection assay, and Mass spectrometry.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LA-PCR, multiplex PCR, touchdown PCR, etc., may be used. Preferably, real-time PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized products become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

"DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found in linear and circular DNA molecules including, but not limited to, restriction fragments, viruses, plasmids, cosmids, and artificial and naturally occurring chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

By the terms "enzymatically amplify" or "amplify" is meant, for the purposes of the specification or claims, DNA amplification by any process by which nucleic acid sequences are amplified in number. There are several means for enzymatically amplifying nucleic acid sequences known in the art. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme Qβ replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified. The particular methodology used to amplify DNA sequences is not intended to be limiting, and all such it is intended that the scope of the invention will include all methods of DNA amplification known in the art.

The "extension of the primers" refers to the addition of nucleotides to a primer molecule so as to synthesize a nucleic acid complementary to a template molecule. "Extension of the primers" does not necessarily imply that the primer molecule is extended to synthesize a complete complementary template molecule. Rather, even if only a fraction of the template molecule has been copied, the primer is still considered extended.

A "fragment" of a molecule such as a protein or nucleic acid is meant to refer to any portion of the amino acid or nucleotide genetic sequence.

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in the case of an RNA molecule) in the fragment sequence, the oligonucleotide sequenced has a T, G, C or A, respectively. The hybridized fragment/oligonucleotide is called a "duplex." In the case of a DNA-RNA hybrid, the molecular is called a "heteroduplex."

A "hybridization complex", means a complex of nucleic acid molecules including at least the target nucleic acid and sensor probe. It may also include an anchor probe.

By "immobilized on a solid support" is meant that a fragment, primer or oligonucleotide is attached to a substance at a particular location in such a manner that the system containing the immobilized fragment, primer or oligonucleotide may be subjected to washing or other physical or chemical manipulation without being dislodged from that location. A number of solid supports and means of immobilizing nucleotide-containing molecules to them are known in the art; any of these supports and means may be used in the methods of this invention.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA. An "isolated" nucleic acid molecule is one that is separated from other nucleic acid molecules that are present in the natural source of the nucleic acid. A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

"Polymerase chain reaction" or "PCR" refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. No. 5,455,175. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

A "polymerase" is an enzyme that catalyzes the sequential addition of monomeric units to a polymeric chain, or links two or more monomeric units to initiate a polymeric chain. In preferred embodiments of this invention, the "polymerase" will work by adding monomeric units whose identity is determined by and which is complementary to a template molecule of a specific sequence. For example, DNA polymerases such as DNA Pol I and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary stands using two primers.

A "polynucleotide" refers to a linear chain of nucleotides connected by a phosphodiester linkage between the 3'-hydroxyl group of one nucleoside and the 5'-hydroxyl group of a second nucleoside, which in turn is linked through its 3'-hydroxyl group to the 5'-hydroxyl group of a third nucleoside and so on to form a polymer comprised of nucleosides liked by a phosphodiester backbone. A "modified polynucleotide" refers to a polynucleotide in which one or more natural nucleotides have been partially or substantially completely replaced with modified nucleotides.

A "primer" is a short oligonucleotide, the sequence of which is complementary to a segment of the template which is being replicated, and which the polymerase uses as the starting point for the replication process. By "complementary" is meant that the nucleotide sequence of a primer is such that the primer can form a stable hydrogen bond complex with the template; i.e., the primer can hybridize to the template by virtue of the formation of base-pairs over a length of at least ten consecutive base pairs.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A "restriction enzyme" refers to an endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to polynucleotide that differs from another polynucleotide by a single nucleotide exchange. For example, without limitation, exchanging one A for one C, G or T in the entire sequence of polynucleotide constitutes a SNP. Of course, it is possible to have more than one SNP in a particular polynucleotide. For example, at one locus in a polynucleotide, a C may be exchanged for a T, at another locus a G may be exchanged for an A and so on. When referring to SNPs, the polynucleotide is most often DNA and the SNP is one that usually results in a change in the genotype that is associated with a corresponding change in phenotype of the organism in which the SNP occurs.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "thermostable polymerase" refers to a DNA or RNA polymerase enzyme that can withstand extremely high temperatures, such as those approaching 100° C. Thermostable polymerases are typically isolated from organisms that live in extreme temperatures, such as *Thermus aquaticus*. Examples of thermostable polymerases include Taq, Tth, Pfu, Vent, deep vent, UITma, and variations and derivatives thereof.

A "variant" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variant" are used interchangeably herein to describe such variants. As used herein, the term "variant" in the singular is to be construed to include multiple variances; i.e., two or more nucleotide additions, deletions and/or substitutions in the same polynucleotide. A "point mutation" refers to a single substitution of one nucleotide for another.

The present invention makes use of a number of oligonucleotide sequences as described herein as primers for use in DNA amplification reaction or as hybridization probes. It is well known to those skilled in the art that such oligonucleotides may be modified in terms of length and even specificity, and they will still be well suited to the practice of the invention. As such, the invention is not limited to the precise oligonucleotides described but is intended to include all those oligonucleotides that will allow the method of the invention to be carried out as disclosed herein.

Introduction:

A variety of characteristics of livestock animals are considered important in determining the overall value of the finished product. Some factors are involved in the palatability of the meat produced, which is important to consumers, and which is reflected in the grading system used to classify meat. Still other factors affect the cost of producing an animal of given size and therefore affect the cost of meat that the consumer will ultimately pay, and which will result in improved profitability for producers of livestock as well as the operators of feedlots. As a result, methods of production that can improve the quality, or reduce the cost of production are desirable for all concerned in the production and consumption of meat from livestock.

The present invention discloses the discovery of SNPs that are associated with a variety of parameters related to the growth rate of animals. Knowledge of the CRH, POMC and MC4R genotype of animals permits the development of genetic testing methods such that animals with the most desirable characteristics with regard to carcass weight, average daily weight gain and rib eye area can be identified and selected. This in turn leads to the development of methods of livestock management, wherein a higher degree of predictability about the eventual development of livestock animals becomes possible, once the genotype of animals with regard to the CRH, POMC and MC4R genes is determined.

According to one aspect of the present invention, there is provided a method for distinguishing *bovines* having a CRH gene polymorphism. The method comprises the steps of first isolating a genomic DNA sample from a *bovine*, and then amplifying a region of the *bovine* CRH gene using an oligonucleotide pair to form nucleic acid amplification products of CRH gene polymorphism sequences. Amplification can be by any of a number of methods known to those skilled in the art including PCR, and the invention is intended to encompass any suitable methods of DNA amplification.

The amplification products are then analyzed in order to detect the presence or absence of at polymorphism in the CRH gene that alters the fourth amino acid and which is associated with a number of desired phenotypes. The polymorphism comprises a C to G transition at a position corresponding to position 22 of SEQ ID NO: 1, which is the cDNA sequence of exon 2 of the *Bos taurus* corticotrophin-releasing hormone precursor (CRH) gene (GenBank Accession No. AF340152). The presence of a "G" residue at this position results in animals that display the desirable phenotypes of increased carcass weight, increased end-of-test rib-eye area and increased post-natal growth. By practicing the method of the present invention and analyzing the amplification products it is possible to determine the genotype of individual animals with respect to the polymorphism.

Conveniently, analysis may be made by restriction fragment length polymorphism (RFLP) analysis of a 129 bp PCR produced by amplification of *bovine* genomic DNA with the oligonucleotide pair of SEQ ID NO: 4 and SEQ ID NO: 5. The use of a forward primer containing a purposeful mismatch, in combination with a target DNA containing the "G" allele, creates a DdeI site such that the presence of the "G" allele is positively indicated by digestion of the amplification products with DdeI. In the absence of the "G" allele, the amplification product still contains a single DdeI site, normally present in the CRH gene, such that digestion yields two fragment of 88 and 41 bp. In the presence of the SNP, the "G" allele, an additional DdeI site is created at nucleotide 87 of the amplification product, resulting in the further digestion of the 88 bp fragment to yield fragments of 69 and 19 bp.

In order to simplify detection of the amplification products and the restriction fragments, it will be obvious to those skilled in the art that the amplified DNA will further comprise labeled moieties to permit detection of relatively small amounts of product. A variety of moieties are well known to those skilled in the art and include such labeling tags as fluorescent, bioluminescent, chemiluminescent, and radioactive or colorigenic moieties.

A variety of methods of detecting the presence and restriction digestion properties of CRH gene amplification products are also suitable for use with the present invention. These can include methods such as gel electrophoresis, mass spectroscopy or the like. The present invention is also adapted to the use of single stranded DNA detection techniques such as fluorescence resonance energy transfer (FRET). For FRET analysis, hybridization anchor and detection probes may be used to hybridize to the amplification products. The probes sequences are selected such that in the presence of the SNP (i.e. a G residue at position 22 as described above), the resulting hybridization. complex is more stable than if there is a C residue at the same position. By adjusting the hybridization conditions, it is therefore possible to distinguish between animals with the SNP and those without. A variety of parameters well known to those skilled in the art can be used to affect the ability of a hybridization complex to form. These include changes in temperature, ionic concentration, or the inclusion of chemical constituents like formamide that decrease complex stability. It is further possible to distinguish animals heterozygous for the SNP versus those that are homozygous for the same. The method of FRET analysis is well known to the art, and the conditions under which the presence or absence of the SNP would be detected by FRET are readily determinable.

It is also well known to those in the art that a number of DNA amplification techniques are suitable for use with the present invention. Conveniently such amplification techniques may comprise methods such as polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification. The precise method of DNA amplification is not intended to be limiting, and other methods not listed here will be apparent to those skilled in the art and their use is within the scope of the invention.

In another aspect, the present invention provides a method for distinguishing *bovines* having a POMC gene polymorphism. The method comprises isolating genomic DNA from a *bovine*, amplifying a region of the *bovine* POMC gene using an oligonucleotide pair to form nucleic acid amplification sequences comprising amplified POMC gene polymorphism sequences, and then analyzing the amplification products in order to detect the presence or absence of a SNP in the POMC gene at position 254 of SEQ ID NO: 2. The polymorphism is a C to T transition, such that the presence of a "T" residue at this position is associated with the desirable phenotypes of increased shipping weight and increased average daily gain, as compared to animals with a "C" residue at position 254 of SEQ ID NO: 2.

Conveniently, the POMC SNP can be detected by restriction digest of a 390 bp amplification product produced using the oligonucleotide pair SEQ ID NO: 6 and SEQ ID NO: 7. The presence of a "T" residue creates a BtsI restriction site at nucleotide 157 in a nucleic acid amplification product produced by amplification of the POMC gene using the oligonucleotide pair SEQ ID NO: 6 and SEQ ID NO: 7. The presence of the SNP is readily detected by digestion of the amplification product with BtsI, and the digestion products analyzed by methods such as gel electrophoresis and the like.

As was described above, in order to simplify detection of the amplification products and the restriction fragments, it will be obvious to those skilled in the art that the amplified DNA will further comprise labeled moieties to permit detection of relatively small amounts of product.

In practicing the present invention it is also possible to use other known methods of analysis, such as FRET analysis, as a method of detection. Conveniently, hybridization probes comprising an anchor and detection probe, the design of which art is well known to those skilled in the art of FRET analysis, are labeled with a detectable moiety, and then under suitable conditions are hybridized a POMC amplification product containing the site of interest in order to form a hybridization complex. Specifically, the hybridization probe will be designed such that a change at position 254 of SEQ ID NO: 2 will produce a hybridization complex of altered stability. A variety of parameters well known to those skilled in the art can be used to affect the ability of a hybridization complex to form. These include changes in temperature, ionic concentration, or the inclusion of chemical constituents like formamide that decrease complex stability.

The presence or absence of the POMC SNP is then determined by the stability of the hybridization complex as was described for the CRH gene. The parameters affecting hybridization and FRET analysis are well known to those skilled in the art. In addition, the foregoing are examples of amplification products and hybridization probes that are suitable for use with FRET analysis. It will be readily apparent to those skilled in the art that modification may be made to the oligonucleotides that are used to synthesize the amplification products or probes while still permitting the practice of the present invention. As before, a variety of amplification methods are suitable for use in the practice of the present invention and all such methods are intended to be within the scope of the invention.

In another aspect, the present invention provides a method for distinguishing animals having a MC4R gene polymorphism. The method comprises isolating genomic DNA from a *bovine*, amplifying a region of the *bovine* MC4R gene using an oligonucleotide pair to form nucleic acid amplification sequences comprising amplified MC4R gene polymorphism sequences, and then detecting a SNP present in the MC4R gene. The SNP comprises a G to C transition at position 1069 of SEQ ID NO: 3, and is associated with the phenotype of maximum increased hot carcass weight, as compared to *bovines* with a "G" residue at this position.

Conveniently, a portion of the MC4R gene is amplified using the oligonucleotide pair SEQ ID NO: 8 and SEQ ID NO: 9, which yields a 226 bp amplification product. The presence of a "T" residue results in an RFLP due to the creation of a TaiI restriction site. Thus, the presence or absence of the SNP in the MC4R gene can be detected by restricting the amplification product with TaiI. In the absence of the SNP the 226 bp is undigested, while in the presence of the SNP, the 226 bp is digested to yield two fragments of 123 and 103 bp. The results of the digestion reaction are analyzed using well-known DNA sizing techniques such as gel electrophoresis and the like. To aid in the detection of the digestion products in cases where small amounts of DNA amplification products are involved, the amplification products may be labeled with a detectable moiety to aid in the sensitivity of the detection methods used. Such labeling tags and methods are known to those skilled in the art and it will be readily apparent whether such modifications would be needed or desired.

Detection of the SNP present in the MC4R gene can also be conveniently performed by FRET analysis. Here the amplification product produced by the oligonucleotide pair SEQ ID NO: 8 and SEQ ID NO: 9 is included in a hybridization reaction with oligonucleotide probes that serve as hybridization anchor and probe sequences. Conveniently, the anchor and probe are labeled such that FRET analysis can be used to detect the presence or absence of the SNP in the MC4R gene. The parameters affecting hybridization and FRET analysis are well known to those skilled in the art. In addition, the foregoing are examples of amplification products and hybridization probes that are suitable for use with FRET analysis. It will be readily apparent to those skilled in the art that modification may be made to the oligonucleotides that are used to synthesize the amplification products or probes while still permitting the practice of the present invention. As before, a variety of amplification methods are suitable for use in the practice of the present invention and all such methods are intended to be within the scope of the invention.

The present invention also describes newly discovered single nucleotide polymorphism sequences, previously not known in the art. In particular, the invention describes nucleic acids comprising a portion of the *bovine* CRH gene, further comprising a polymorphism at position 22 as defined by the positions in SEQ ID NO: 1, and in which there is a "C" residue at position 22. The invention also describes a nucleic acid comprising a portion of the *bovine* POMC gene, in which a T residue is present at position 254 as defined by the positions in SEQ ID NO: 2.

Conveniently, purified and isolated nucleic acids comprising the SNPs of the invention may be recovered from animals by subjecting a sample of genomic DNA to an amplification procedure. Alternatively, it will be readily apparent to those skilled in the art that DNA segments containing the SNP could be artificially produced by oligonucleotide synthesis technology, or by screening cDNA or genomic DNA libraries produced from animals known to possess the polymorphisms.

*Bovines*, like all mammals, are diploid organisms possessing pairs of homologous chromosomes. Thus, at a typical genetic locus, an animal has three possible genotypes that can result from the combining of two different alleles (e.g. A and B). The animal may be homozygous for one or another allele, or heterozygous, possessing one of each of the two possible alleles (e.g. AA, BB or AB).

The present invention provides a method of selecting individual livestock animals based on the knowledge of an animal's CRH genotype. With respect to the SNP described in the present invention, the two possible alleles are a "C" or "G" residue at position 22 as defined by SEQ ID NO: 1. The method of the invention comprises the steps of determining the CRH alleles of an animal, such that it can be determined whether an animal is "CC", "CG" or "GG" with respect to the CRH gene locus. The presence of a "G" allele is associated the desired phenotypes. With the knowledge of the animal's genotype one can then identify and sort animals into groups of like phenotype, or otherwise use the knowledge of the genotype in order to predict which animals will have the desired phenotypes of increased hot carcass weight, increased end-of-test rib-eye area and increased adjusted weaning weight, a measure of post-natal growth.

Here sorting can be taken to mean placing animals in physical groupings such as pens, so that animals of like genotype are kept separate from animals of a different genotype. This would be a useful practice in the case of breeding programs where it would be desirable to produce animals of particular genotypes. For example, it may be desirable to establish herds that are homozygous "GG" at the CRH gene, such that breeding among these animals would only produce more "GG" animals. Here keeping animals of this genotype separate would be needed to ensure that "GG" animals did not have the opportunity to breed with animals possessing one or more "C" alleles, which could result in the reproduction of animals with a reduced tendency to display the desired phenotypes associated with the CRH "G" allele. Furthermore, by ensuring that at least one animal in a breeding pair is "GG" at the CRH locus, conveniently allows for the frequency of the "G" allele to be increased in the next, and subsequent generations.

Sorting may also be of a "virtual" nature, such that an animal's genotype is recorded either in a notebook or computer database. Here, animals could then be selected based on their known genotype without the need for physical separation. This would allow one to select for animals of desired phenotype where physical separation is not required.

The invention further provides a method of selecting individual livestock animals based on the knowledge of an animal's POMC genotype. With respect to the POMC SNP described in the present invention, the two possible alleles are a "C" or "T" residue at position 254 as defined by SEQ ID NO: 2. The method of the invention comprises the steps of determining the POMC alleles of an animal, such that it can be determined whether an animal is "CC", "CT" or "TT" with respect to the POMC gene locus. With the knowledge of the animal's genotype one can then sort animals into groups of like phenotype, or otherwise use the knowledge of the genotype in order to predict which animals will have the desired phenotypes of increased shipping weight, increased average daily gain and increased hot carcass weight. The extent of the phenotypic response is directly related to the number of "T" alleles, such that an animal homozygous for the "T" allele, a "TT" animal, will display the greatest phenotypic change for the desired phenotypes when compared to animals with the "CC" genotype. Animals that are "CT" display an intermediate phenotypic response.

As described for the CRH gene, knowledge of the POMC genotype allows for the selection and sorting of animals that will display desired phenotypes. As before, sorting may be physical or virtual, and may be used in conjunction with animal breeding or other herd management programs.

The invention further comprises a method of selecting individual livestock animals based on the knowledge of an animal's MC4R genotype. With respect to the MC4R SNP described in the present invention, the two possible alleles are a "C" or "G" residue at position 1069 as defined by SEQ ID NO: 3. The method of the invention comprises the steps of determining the MC4R alleles of an animal, such that it can be determined whether an animal is "CC", "CG" or "GG" with respect to the MC4R gene locus. The presence of a "C" allele is associated the desired phenotypes of increased hot carcass weight. With the knowledge of the animal's genotype one can then sort animals into groups of like phenotype, or otherwise use the knowledge of the genotype in order to predict which animals will have the desired phenotypes of increased hot carcass weight.

Knowledge of an animal's MC4R genotype provides a further advantage. Animals with one or two "C" alleles will display an increase in hot carcass weight, regardless of the animal's CRH genotype. Thus, where the sole phenotype of interest is increased hot carcass weight, selecting animals with either the "GG" CRH genotype or the "CC" or "CG" MC4R genotypes will accomplish the same goal, being the greatest increase in hot carcass weight. Any animals that have at least one "C" allele at the MC4R gene locus will display the increased hot carcass weight phenotype, and thus testing of animals for the presence of the CRH SNPs will not be necessary to detect and select the desired animals.

For the sub-group of animals that lack a "C" allele at MC4R, further testing for the presence of CRH SNP could detect additional animals that will display the desired phenotype. In any population where the "C" and "G" alleles for the MC4R gene are both present, testing for MC4R genotype provides the greatest chance of detecting animals that will display the maximum increased hot carcass weight possible. This occurs because two out of three possible combinations will have a "C" allele. In contrast, only one in three of the possible combinations, "GG", in the CRH SNP will exhibit the same maximum increase in hot carcass weight. The overall advantage will be that fewer animals will need to be tested for both CRH and MC4R genotypes if the MC4R genotype of the animal is determined first. Thus, based on the allele frequencies shown in Table V, it is more likely that an animal will have at least one "C" allele at MC4R than that it will be homozygous for the "G" allele at CRH.

As described for the CRH and POMC genes, knowledge of an animal's MC4R genotype allows for the selection and sorting of animals that will display desired phenotypes. As before, sorting may be physical or virtual, and may be used in conjunction with animal breeding or other herd management programs.

It is a further aspect of the invention that animals can be selected as to their combined CRH and POMC genotypes. There is an advantage to selecting animals with a "GG" genotype at the CRH gene locus, and a "TT" genotype at the POMC gene locus, in that animals that are double homozygotes ("GG-TT" animals) will display the greatest phenotypic change in the desirable phenotypes of increased hot carcass weight, increased shipping weight, increased average daily gain and increased end-of-test rib-eye area, greater than that which would be obtained for animals homozygous for only one of the CRH and POMC loci. Thus, through the method of the invention, animals with the most desirable combination of growth-related phenotypes can be selected. As before, the selection may be physical or virtual, and the advantage of selecting animals based on their combined CRH and POMC genotypes will be readily apparent to those skilled in the areas of animal breeding, herd management and the like.

In order to fully realize the utility of the invention, there are also provided diagnostic kits that can be used to determine the CRH, POMC or MC4R genotypes of animals. In general, each of the kits comprises oligonucleotide primers suitable to amplify the portions of each gene comprising the SNPs of the present invention. The kits comprise forward and reverse primers suitable for amplification of a DNA sample taken from an animal. The sample may be from any tissue or fluid in which genomic DNA is present. Conveniently the sample may be taken from blood skin or a hair bulb.

To for the presence of CRH SNP alleles, the kit comprises a forward primer comprising at it's 3' end sequence identical to at least 10 contiguous nucleotides within SEQ ID: 1, a reverse primer comprising at it's 3' end a nucleotide sequence fully complementary to at least 10 contiguous nucleotides with SEQ ID NO: 1. The primers are preferably from 10 to 30 nucleotides in length, although variation in the length of the primer is not intended to be limiting. An example of suitable primers would be those defined by SEQ ID NO: 4 and SEQ ID NO: 5.

In one embodiment of a diagnostic kit, the primers will be used to amplify DNA from a genomic DNA sample to produce amplification products, which can then be analyzed by restriction digest for the presence or absence of the SNP at position 22 as defined by SEQ ID NO: 1. In an alternative embodiment, the kit would further comprise hybridization probes adapted to distinguish between the two CRH alleles using FRET analysis. In this embodiment, the use of FRET analysis is one such method well known in the art that is suitable for detecting SNPs. Where a method of analysis such as FRET is used, the hybridization probes would be labeled with a detectable moiety to aid in the detection of the SNP. The types of detectable moieties suitable for use in FRET analysis are well known to those skilled in the art of molecular biology.

In another embodiment, where it is desired to test for the presence of POMC SNP alleles, the kit comprises a forward primer comprising at it's 3' end sequence identical to at least 10 contiguous nucleotides within SEQ ID: 2, a reverse primer comprising at it's 3' end a nucleotide sequence fully complementary to at least 10 contiguous nucleotides with SEQ ID NO: 2. The primers are preferably from 10 to 30 nucleotides in length, although variation in the length of the primer is not intended to be limiting. An example of suitable primers would be those defined by SEQ ID NO: 6 and SEQ ID NO: 7.

In one embodiment of a diagnostic kit, the primers will be used to amplify DNA from a genomic DNA sample to produce amplification products, which can then be analyzed by restriction digest for the presence or absence of the SNP at position 254 as defined by SEQ ID NO: 2. In an alternative embodiment, the kit would further comprise hybridization anchor and detection probes adapted to distinguish between the two POMC alleles using FRET analysis. Where a method of analysis such as FRET is used, the hybridization probes would be labeled with a detectable moiety to aid in the detection of the SNP. The types of detectable moieties suitable for use in FRET analysis are well known to those skilled in the art of molecular biology.

In yet another embodiment, where it is desired to test for the presence of MC4R SNP alleles, the kit comprises a forward primer comprising at it's 3' end sequence identical to at least 10 contiguous nucleotides within SEQ ID: 3, a reverse primer comprising at it's 3' end a nucleotide sequence fully complementary to at least 10 contiguous nucleotides with SEQ ID NO: 3. The primers are preferably from 10 to 30 nucleotides in length, although variation in the length of the primer is not intended to be limiting. An example of suitable primers would be those defined by SEQ ID NO: 8 and SEQ ID NO: 9.

In one embodiment of a diagnostic kit, the primers will be used to amplify DNA from a genomic DNA sample to produce amplification products, which can then be analyzed by restriction digest for the presence or absence of the SNP at position 1069 as defined by SEQ ID NO: 3. In an alternative embodiment, the kit would further comprise hybridization probes adapted to distinguish between the two MC4R alleles by FRET analysis. In this embodiment, the use of FRET analysis is one such method well known in the art that is suitable for detecting SNPs. Where a method of analysis such as FRET is used, the hybridization probes would be labeled with a detectable moiety to aid in the detection of the SNP. The types of detectable moieties suitable for use in FRET analysis are well known to those skilled in the art of molecular biology.

It will also be obvious to one skilled in the art that diagnostic kits will include additional reagents including, but not limited to lysing buffers for lysing cells contained in a sample, dNTP's, reaction buffer, an amplifying enzyme and combinations thereof. Kits may also include accessory diagnostic agents such as the restriction enzyme used to detect the SNP, or detection reagents to reveal the presence of detectable moieties. For example, it is well known in the art, and especially where only limited quantities of DNA are available, to use sensitive detection techniques such as Southern blot hybridization, chromatography or mass spectroscopy in order to detect specific amplification products, or specific restriction digest products derived from amplification products as derived herein. Thus, the precise means of detecting the various SNPs from the amplification or restriction digest products could be performed by a variety of techniques well known to those skilled in the art of molecular biology, and the present invention is intended to encompass those methods of detection.

The diagnostic kits as referred to herein may be individually packaged for each individual gene locus to be tested, or the required reagents required to test for polymorphisms in all three genes could be present in a single kit. Such variation is common in diagnostic kits and it not intended to be limiting of the invention.

EXAMPLES

In terms of demonstrating the practice of the inventions the following examples are provided.

Materials and Methods:

Cattle:

A group of 256 tan-colored Charolais-cross steers were divided into two groups of 128 animals each, and either limit-fed a grain diet or full-fed a forage-based diet during the backgrounding phase (90 day period). During the finishing phase each of these two groups were divided into half and allowed a full or limited high grain diet; this was based on voluntary intake. The full diets were 100% ad libitum and the limited diets were 95% ad libitum. Live animal weight, ultrasound measurements of rib-eye area (REA) and average daily gain (ADG) data were collected. Steers were sent for slaughter as they approached a target shipping weight of 635 kg (mean=636.6 kg, SD=21.48). They were weighed every two weeks then on two consecutive days and transported for slaughter within a week where hot carcass weight (HCW) data was collected Adjusted weaning weights were available in a second group of animals (n=255) that included the Canadian Beef Reference Herd (n=132; Schmutz et al., 2001) and 123 animals from three ranches.

SNP Identification in CRH Gene:

Exon 2 of the CRH gene was amplified and sequenced as described in Buchanan et al. (2002b; GenBank accession number AF340152). Briefly, the following single-stranded DNA primers were used to amplify a 254 bp fragment:

```
Forward:
5'-ATGCGACTGCCGCTGCTCG-3'

Reverse:
5'-AGAGAGGGGAGCAGCCCG-3'
```

The 20 ul reaction contained: 100 ng of DNA, 10× PCR buffer, 5× Q-solution (Qiagen), 0.2 mM dNTPs, 0.5 units Taq polymerase, 4 pmol forward primer, and 4 pmol reverse primer. The amplification program consisted of one cycle of 95° C. for 2 minutes, followed by 35 cycles of: denaturation at 95° C. for 45 sec, annealing at 55° C. for 30 sec and extension at 72° C. for 45 sec, followed by a final cycle of extension at 72° C. for 3 minutes. Sequencing of PCR products was performed on an AB1373 sequencer (Applied Biosystems). Sequence was aligned and compared for variation using Sequencher 4.1.2 (Gene Codes Corporation).

PCR-RFLP Analysis:

CRH4

The CRH4 SNP is defined by a C to G transition at position 22 of SEQ ID NO: 1. Wherever the term "CRH4" or "CRH4 SNP" is used it is meant to refer to the nucleotide present at position 22 of SEQ ID NO: 1. CRH4 genotypes were derived from the amplification and subsequent digestion of the product with DdeI (New England BioLabs). The following primers were used to amplify a 129 bp product:

```
Forward:
5'-GCGCCCGCTAAAATGCGACTGA-3'

Reverse:
5'-CTGTGATGCCTGCCGGGCAC-3'
```

The 25 ul amplification reaction contained 50 ng of genomic *bovine* DNA, 0.2 uM of each primer, 0.2 mM dNTPs, 45 mM Tris-HCl pH 8.8, 11 mM $(NH_4)_2SO_4$, 4.5 mM $MgCl_2$, 6.7 mM β-mercaptoethanol, 4.5 mM EDTA, 0.25 mM spermidine, 10% DMSO and 0.65 U Taq DNA polymerase (Invitrogen). The cycling protocol was 2 min at 94° C., 35 cycles of 94° C. for 1 min, 62° C. for 45 sec, 72° C. for 50 sec, with a final extension at 72° C. for 4 min. A 4 min. A 2-hour digestion with DdeI was carried out in a 37° C. water bath. The digested PCR-products were separated on a 4% agarose gel. Digestion of the 129 bp PCR product with DdeI produced fragments of 88 and 41 bp, due to the presence of a DdeI recognition site at nt 87 of the PCR product. This site was present in the DNA of all animals tested. The CRH4 SNP introduces a second DdeI recognition site due the presence of a G residue at nucleotide 87, resulting in further digestion of the 88 bp fragment further into fragments of 69 and 19 bp upon digestion with DdeI.

POMC, LEP and MC4R Genotyping:

Genotyping methods for SNPs present in POMC, MC4R and LEP have previously been described (Buchanan et al., 2002a; 2002b; Thue et al., 2003).

Statistical Analysis:

A regression analysis was carried out in the group of 255 cattle to determine if the number of copies of a CRH allele significantly affected adjusted weaning weight. In the steers (fed two different backgrounding rations and finishing diets) statistical analyses were performed using the general linear model (GLM) procedure of SAS (SAS, 1998). No significant effects were observed based on backgrounding (forage vs. grain) or finishing (limited vs. ad libitum) diets or the interaction between the two and hence these were deleted from the model. No significant effects were observed with leptin or between the four or three gene interactions and hence these were deleted from the model.

In steers, the model used to determine the effects of genotype on ADG, EOT-REA, shipping weight and HCW was:

$$Y_{kmno} = \mu + GCRH_k + GPOMC_m + GMC4R_n + GCRH \times GPOMC_{km} + GCRH \times GMC4R_{kn} + GPOMC \times GMC4R_{mn} + e_{kmno}$$

Where: $Y_{kmno}$ is an observation of the dependent variable (end-of-test REA, Shipping weight, hot carcass weight (HCW) and average daily gain (ADG)); $\mu$ is the overall population mean for the variable; $GCRH_k$ is the effect of the kth genotype of CRH4 (k=1 (GC), 2 (CC), 3 (GG)); $GPOMC_m$ is the effect of the mth genotype of POMC (m=1 (CC), 2 (CT), 3 (TT)); GMC4R is the effect of the nth genotype of MC4R (n=1 (GG), 2 (GC), 3 (CC)); GCRH×GPOMC$_{km}$, GCRH× GMC4R$_{kn}$, and GPOMC×GMC4R$_{mn}$ are effects of the gene interaction and $e_{kmno}$ is the random error associated with the observation. Treatments comparisons used least squares means by PDIFF options (SAS, 1998). Significance was declared at P<0.05.

Results:

The CHR4, POMC, MC4R and LEP genes were genotyped in 256 steers and then analyzed using GLM for association with average daily gain (ADG), end-of-test rib-eye area (EOT-REA), shipping weight and hot carcass weight (HCW). The CRH4 SNP was positively correlated with EOT-REA and HCW (Table I). The POMC SNP was positively correlated with shipping weight and HCW and there was evidence of a trend associated with ADG (Table I). MC4R showed a trend with HCW (Table I).

Interactions between two sets of genes were observed in the case of two traits. The CRH and POMC genes appeared to interact with respect to EOT-REA (P=0.0407), while the CRH and MCR4 genes appeared to interact with respect to HCW (P=0.02) (Table I).

In the case of the interaction between the CRH and MCR4 genes, HCW increased by 26 kg where animals were homozygous at CRH for the "C" allele, and had either one or two MC4R "C" alleles (i.e. "CC" or "CG" at the MCR4 SNP site) as compared to animals with an MC4R "GG" genotype (P=0.008 and P=0.008). However, these same animals (CC-CC or CC-CG at MCR4) were not significantly different from animals that had one or two "G" alleles at CRH.

The data lead to the conclusion that, if an animal has either the "GG" genotype at the CRH gene locus, or, at least one "C" allele at the MC4R gene locus, then they will display the desired phenotype of increase hot carcass weight. Thus, CRH and MC4R operate as parallel switches with respect to the increased hot carcass weight phenotype such that if one switch is on, the position of the other is irrelevant.

Carcass yield least square means for CRH and POMC genotypes are reported in Tables II and III respectively. The presence of a "G" allele at CRH4 is associated with an increase in weight. In the case of POMC, the "T" allele is associated with increased weights. Furthermore, the effect of a "T" allele appears to be additive with each copy of the allele resulting in an increase of 9 kg. The "C" allele at MC4R is associated with an increase in HCW (LS Means CC=378, CG=377 and GG=368 SEM=1.79), and acts in a dominant fashion.

The expected gains in cm$^2$ of rib-eye area or live and carcass weight in kilograms are shown in Table IV. Allele frequencies observed in the 256 steers for CRH4, POMC and MC4R are shown in Table V. The allele frequencies were such that adequate representation of all genotypes would have been present in the test population.

Three SNPs have now been identified in the CRH gene, two in the pro-peptide region and another in the signal sequence. The C/G SNP at codon 4 of CRH (position 22 of SEQ ID NO: 1) appears to be the mutation associated with effects on adjusted weaning weight, a measure of post-natal growth and carcass weight. A Pro within the CRH signal sequence at codon 4 has been previously reported in both sheep (Roche et al., 1988) and humans (Shibabara et al., 1983). Similarly, in the Genbank database a Pro at this same site has been reported in another *ovine* sequence, two *porcine*, and two more human CRH sequences (Accession Numbers J00803, AF440229, Y15159, NM000756 and BC011031 respectively).

Figure 3:
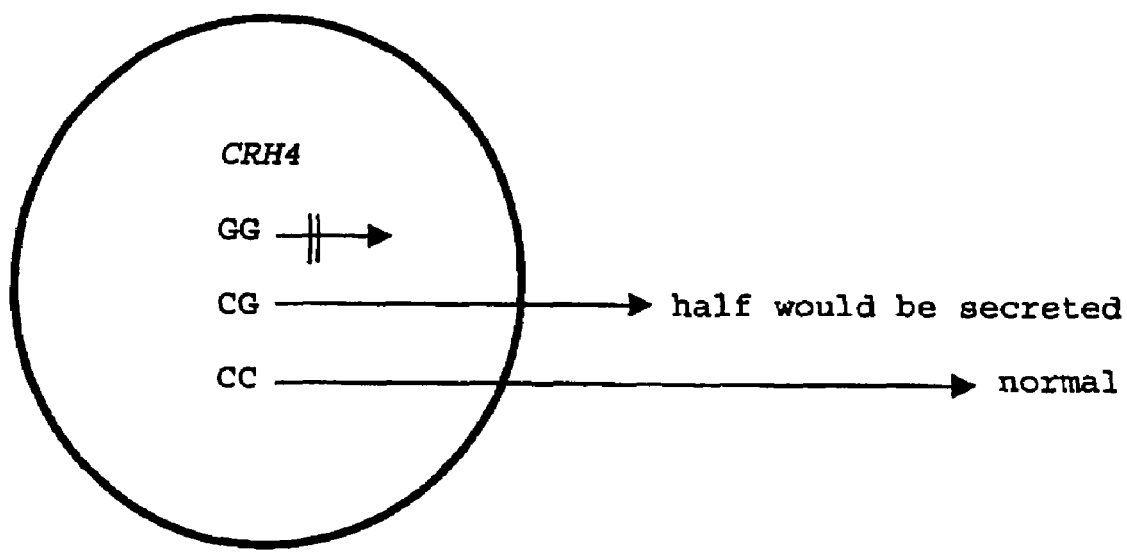
FIG. 3: The effect of CRH genotype on CRH secretion.

The introduction of an Arg at position 4 in the signal sequence could lead to a reduction in the levels of circulating CRH (FIG. 3), resulting in a decrease in the growth inhibition effect normally associated with this hormone.

The data indicate that the CRH4 SNP is predictive of increased EOT-REA and HCW. The data from animals that were "GG-TT" homozygotes at CRH and POMC respectively, suggests that the presence of the CRH4 allele does not result in an increase in shipping weight above that observed for POMC "TT" homozygotes alone. The data from animals with various CRH and MC4R genotypes showed that the greatest increase in hot carcass weight could be achieved either by having CRH animals homozygous for the "G" allele SNP, or animals with at least one "C" allele at the MC4R locus.

We had previously sequenced POMC as a candidate gene for ADG and carcass weight. We mapped it directly under QTL peaks (Thue et al., 2003) and the current results confirm its association with ADG (P=0.07) and carcass weight. Whatever the molecular mechanism through which POMC polymorphisms act, the associations with increased ADG, shipping and hot carcass weight can be capitalized upon by selecting cattle that are homozygous for the "T" allele at POMC. The effect seen on shipping weight is likely to be an under estimate, based on how these animals were shipped (target weight) as compared to the usual practice. The usual practice in feedlots is to either use a set number of days on feed or visually appraise the weight of an animal, and then actually weigh a truckload of cattle.

Since CRH affects POMC levels both directly in the hypothalamus, and indirectly by affecting the release of glucocorticoids, it was important to determine if the associations between these genes and the various traits we have examined were dependent or independent effects of the SNPs that have been studied. As there was no interaction effect observed with respect to HCW, the data are consistent with the premise that these genes act independently of each other. As a result, testing for the presence of either the CRH or POMC SNPs will be useful as a predictor of HCW. In addition, given that the allele frequencies of each of the alleles associated with the most desirable traits (increase weights) are fairly common (0.37 for the CRH4 "G" allele, and 0.23 for the POMC "T" allele), it will be possible to use the genetic tests of the present invention to select for animals that are homozygous for both the CRH4 G and POMC "T" alleles. Selecting for such "GG-TT" animals will allow for the concurrent improvement REA, shipping weight, HCW and ADG. Finally, the association observed between adjusted weaning weight and the CRH4 SNP means the cow-calf producer will benefit from genetic selection methods based on this SNP.

TABLE I

General Linear Model Probability values for gene(s) with Trait Associations.

| Gene or Gene interaction | ADG | EOT-REA | Shipping | HCW |
|---|---|---|---|---|
| CRH4 | 0.37 | 0.034* | 0.35 | 0.0015** |
| POMC | 0.07 | 0.45 | 0.0078** | 0.006** |
| MC4R | 0.88 | 0.78 | 0.60 | 0.085 |
| CRH4 × POMC | 0.89 | 0.047* | 0.63 | 0.17 |
| CRH4 × MC4R | 0.28 | 0.46 | 0.21 | 0.02* |

\* = $P < 0.05$;
\*\* = $P < 0.01$

TABLE II

Effects of CRH4 on beef cattle performance (LS means)

| Trait | CC | GC | GG | SEM* |
|---|---|---|---|---|
| EOT-REA | 88.6b | 92.7ab | 94.6a | 0.84 |
| Shipping Wt | 631.5 | 638.5 | 641.5 | 2.55 |
| HCW | 367.5c | 373.7bc | 381.8a | 1.64 |

*SEM = pooled standard error of mean; Means with different letters in the same row are significantly different ($P < 0.05$)

TABLE III

Effects of POMC on beef cattle performance (LS means)

| Trait | CC | CT | TT | SEM* |
|---|---|---|---|---|
| ADG | 1.62 | 1.69 | 1.72 | 0.028 |
| EOT-REA | 92.5 | 93.3 | 90.2 | 1.11 |
| Shipping Wt | 628.0 b | 637.4 a | 646.0 a | 3.37 |
| HCW | 368.8 b | 376.2 a | 378.0 a | 2.16 |

*SEM = pooled standard error of mean; Means with different letters in the same row are significantly different ($P < 0.05$)

TABLE IV

Increase in REA and pounds expected from selecting animals GG at CRH4 or TT at POMC or both GG and TT.

| Trait | CRH4 | POMC | CRH4 + POMC |
|---|---|---|---|
| EOT REA | 6 cm² | — | 6 cm² |
| Ship weight | | 18 kg | 18 kg |
| Hot carcass weight | 14.3 kg | 9.2 kg | 23.5 kg |

TABLE V

Allele frequencies for CRH, POMC and MC4R

| CRH4 | POMC | MC4R |
|---|---|---|
| G = 0.37 | T = 0.23 | C = 0.66 |
| C = 0.63 | C = 0.77 | G = 0.34 |

TABLE VI

Summary of the Phenotypes Associated with the CRH, POMC and MC4R SNPs.

| Gene | SNP | Phenotype(s) |
|---|---|---|
| CRH | C-G transition | HCW, EOTREA, AWW |
| POMC | C-T transition | ADG, HCW, SW |
| MC4R | G-C transition | HCW |

The following abbreviations are used in the tables:
HCW—hot carcass weight;
EOTREA—end of test rib eye area;
AWW—adjusted weaning weight;
ADG—average daily gain;
SW—shipping weight.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

REFERENCES CITED

1. Bagley C. P., Morrison D. G., Feazel J. I., Saxton A. M., Growth and sexual characteristics of suckling beef calves as influenced by age at castration and growth implants, J. Anim. Sci. 67 (1989) 1258-1264.
2. Barendse W., Vaiman D., Kemp S. J., Sugimoto Y., Armitage S. M., Williams J. L., Sun H. S., Eggen A., Agaba M., Aleyasin S. A., Band M., Bishop M. D., Buitkamp J., Byrne K., Collins F., Cooper L., Coppettiers W., Denys B., Drinkwater R. D., Easterday K., Elduque C., Ennis S., Erhardt G., Ferretti L., Flavin N., Gao Q., Georges M., Gurung R., Harlizius B., Hawkins G., Hetzel J., Hirano T., Hulme D., Jorgensen C., Kessler M., Kirkpatrick B. W., Konfortov B., Kostia S., Kuln C., Lenstra J. A., Leveziel H., Lewin H. A., Leyhe B., Lil L., Martin Burriel I., McGraw R. A., Miller J. R., Moody D. E., Moore S. S., Nakane S., Nijman I. J., Olsaker I., Pomp D., Rando A., Ron M., Shalom A., Teale A. J., Thieven U., Urquhart B. G. D., Vage D-I., Van de Weghe A., Varvio S., Velmala R., Vilkki J., Weikard, R., Woodside C., Womack J. E., Zanotti M., Zaragoza P., A medium-density genetic linkage map of the *bovine* genome, Mammal. Genome 8 (1997) 21-28.
3. Buchanan F. C., Thue T. D., Winkelman-Sim D. C., Plante Y., Schmutz S. M., Two QTLs for growth map to *bovine* chromosome 14, 27th International Conference on Animal Genetics, Jul. 22-26 2000, Minneapolis, Minn.
4. Buchanan F. C., Fitzsimmon C. J., Van Kessel A. G., Thue T. D., Winkelman-Sim D. C., Schmutz S. M., Association of a missense mutation in the *bovine* leptin gene with carcass fat content and leptin mRNA levels, Genet. Sel. Evol. 34 (2002) 105-116.
5. Buchanan F. C., Thue T. D., Elsaesser E. D., Winkelman-Sim D. C., A corticotrophin-releasing hormone polymorphism associated with post-natal growth in Beef 6. Dunn A. J., Berridge, C. W., Physiological and behavioral responses to corticotropin-releasing factor administration: is CRF a mediator of anxiety or stress responses? Brain Research Reviews 15 (1990) 71-100.
7. Grobet L., Poncelet D., Royo L. J., Brouwers B., Pirotiin D., Michaux C., Menissier F., Zanotti M., Dunner S., Georges, M., Molecular definition of an allelic series of mutations disrupting the myostatin function and causing double-muscling in cattle, Mammal. Genome 9 (1998) 210-213.
8. Houseknecht K. L., Baile C. Z., Matteri R. L., Spurlock M. C., The biology of leptin: A review, J. Anim. Sci. 76 (1998) 1405-1420.
9. Kress D. D., Burfening P. J., Miller P. D., Vaniman D., Beef sire expected progeny differences calculated by three methods, J. Anim. Sci. 44 (1977) 195-202.
10. Liu H-X., Chew S. L., Cartegni L., Zhang M. Q., Krainer A. R., Exonic splicing enhancer motif recognized by human SC35 under splicing conditions, Molecular and cellular biology 20 (2000)1063-1071.
11. Liu H-X., Cartegni L., Zhang M. Q., Krainer A. R., A mechanism for exon skipping caused by nonsense or missense mutations in BRCA1 and other genes, Nat. Genet. 27 (2001) 55-58.
12. Marsh D. J., Hollopeter G., Huszar D., Laufer R., Yagaloff K. A., Fisher S. L. Burn P. Palmiter R. D., Response of melanocortin-4 receptor-deficient mice to anorectic and orexigenic peptides, Nat. Genet. 21 (1999) 119-122.
13. Pritchard L. E., Tumbull A. V., White A., Pro-opiomelanocortin processing in the hypothalamus: impact on melanocortin signalling and obesity, J. Endocrinol. 172 (2002) 411-421.
14. Roche P. J., Crawford R. J., Fernley R. T., Tregear G. W., Coghlan, J. P., Nucleotide sequence of the gene coding for *ovine* corticotropin-releasing factor and regulation of its mRNA levels by glucocorticoids, Gene 71 (1988) 421-431.
15. SAS (1998) SAS/STAT User's Guide (Release 8.02). SAS Inst. Inc., Cary, N.C.
16. Schmutz S. M., Buchanan F. C., Winkelman-Sim D. C., Pawlyshyn V., Plante Y., McKinnon J. J., Fournier, B. P., Development of the Canadian Beef Reference Herd for gene mapping studies, Theriogenology 55 (2001) 963-972.
17. Schumann F. J., Janzen E. D., McKinnon, J. J., Prophylactic tilmicosin medication of feedlot calves at arrival, Can. Vet. J. 31 (1990) 285-288.
18. Sharpe P. M., Haynes N. B., Buttery P. J., Glucocorticoid status in growth, in: Buttery P. J., Haynes N. B., Lindsay D. B. (Eds.), Control and Manipulation of Animal Growth, Butterworths, London, 1986, p 207-222.
19. Shibahara S., Morimoto Y., Furutani Y., Notake M., Takahashi H., Shimizu S., Horikawa S., Numa, S., Isolation and sequence analysis of the human corticotropin-releasing factor precursor gene, EMBO J. 2 (1983) 775-779.
20. Szabo G., Dallmann G., Muller G., Patthy L., Soller M., Varga, L., A deletion in the myostatin gene causes the compact (Cmpt) hypermuscular mutation in mice, Mammal. Genome. 9 (1998) 671-672.
21. Thue T. D., Schumtz S. M., Buchanan, F. C., A SNP in the cattle MC4R gene is used to map MC4R to BTA 24, Anim. Genet. 32 (2001) 390-391.
22. Thue T. D., Buchanan, F. C., Linkage mapping of POMC to *bovine* chromosome 11, Anim. Genet. 34 (2003) 149.

We claim:

1. A method for distinguishing *bovines* that have an increased shipping weight, increased average daily gain and increased hot carcass weight, comprising:
   isolating genomic DNA from a *bovine*;
   amplifying a region of the bovine POMC gene using an oligonucleotide pair to form nucleic acid amplification sequences comprising amplified POMC gene polymorphism sequences;
   detecting a polymorphism present in the POMC gene at position 254 of SEQ ID NO: 2;
   analyzing the polymorphism, and
   wherein the presence of a "T" residue distinguishes a bovine having an increased shipping weight, increased average daily gain and increased hot carcass weight, as compared to *bovines* with a "C" residue at position 254 of SEQ ID NO: 2.

2. The method of claim 1 wherein the oligonucleotide pair comprises SEQ ID NO: 6 and SEQ ID NO: 7.

3. The method of claim 2 wherein the polymorphism detected is a restriction fragment length polymorphism (RFLP).

4. The method of claim 3 wherein the RFLP is the presence or absence of a BtsI restriction site in a nucleic acid amplification product produced by amplification of the POMC gene.

5. The method of claim 1 further comprising the inclusion of a detectable moiety such that the amplification product comprises a labeled amplification product.

6. The method of claim 5 wherein the detectable moiety is selected from the group consisting of fluorescent, bioluminescent, chemiluminescent, radioactive and colorigenic moieties.

7. The method of claim 1 further comprising:
   contacting the nucleic acid amplification product with a hybridization probe;
   wherein the hybridization probe comprises at least one oligonucleotide labeled with a detectable moiety;
   under suitable conditions permitting hybridization of the at least one oligonucleotide to the amplification product to form a hybridization complex; and
   wherein the presence of the detectable moiety in the hybridization complex indicates the presence of a POMC polymorphism.

8. The method of claim 1 wherein the nucleic acid amplification product is produced by an amplification method selected from the group of polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification.

9. A method of selecting, for *bovines* that have an increased shipping weight, increased average daily gain and increased hot carcass weight, comprising the steps of:
   determining the POMC alleles of an animal;
   wherein the alleles of an animal will be one of "CC", "CT", or "TT" at position 254 of SEQ ID NO: 2; and
   selecting those animals with a "CT" or "TT" genotype, which genotype is associated with the desired phenotypes of increased shipping weight, increased average daily gain and increased hot carcass weight.

* * * * *

SEQUENCE LISTING

```
<160> NUMBER OF SEQ ID NOS: 9

<210> SEQ ID NO 1
<211> LENGTH: 584
<212> TYPE: DNA
<213> ORGANISM: Bos taurus
<220> FEATURE:
<221> NAME/KEY: misc_feature
<222> LOCATION: (22)...(22)
<223> OTHER INFORMATION: SNP present (CRH4")
<220> FEATURE:
<221> NAME/KEY: misc_feature
<222> LOCATION: (145)...(145)
<223> OTHER INFORMATION: SNP present ("CRH 45")
<220> FEATURE:
<221> NAME/KEY: misc_feature
<222> LOCATION: (240)...(240)
<223> OTHER INFORMATION: SNP present ("CRH77")
<300> PUBLICATION INFORMATION:
<308> DATABASE ACCESSION NUMBER: GenBank AF340152
<309> DATABASE ENTRY DATE: 2004-02-12

<400> SEQUENCE: 1
cgcccgctaa aatgcgactg ccgctgctcg tgtccgtggg cgtcctgctg gtggctctgc      60
tgccctcccc gccatgcagg gccctcctca gccgggggcc catcccgggt gcccggcagg     120
catcacagca cccccagccc ctgagtttct tccagccgcc gccgcagccc caggaacccc     180
```

```
aggctctgcc cacccctactc cgtgttgggg aggaatactt cctccgcctg ggtaacctcg   240
atgagacccg ggctgctccs ctctctcccg ccgcctcgcc tctcgccagc agaagcagca   300
gtcgcctttc tccggacaag gtggccgcca acttttttcg agcgctgctg cagccccggc   360
gcccattcga cagcccagcg ggtcccgcgg aacgcggcac ggagaacgcc ctcggcagcc   420
gccaggaggc gccggccgcc aggaagaggc gatcccagga acctcccatc tccctggatc   480
tcaccttcca cctcctccga gaagtcttgg aaatgaccaa ggccgatcag ttagcacagc   540
aagctcatar caayaggaaa ctgttggaca ttgctgggaa atga                    584
```

```
<210> SEQ ID NO 2
<211> LENGTH: 1002
<212> TYPE: DNA
<213> ORGANISM: Bos taurus
<220> FEATURE:
<221> NAME/KEY: misc_feature
<222> LOCATION: (254)...(254)
<223> OTHER INFORMATION: SNP
<300> PUBLICATION INFORMATION:
<308> DATABASE ACCESSION NUMBER: GenBank J00021
<309> DATABASE ENTRY DATE: 1994-10-30

<400> SEQUENCE: 2
gcggagggag tggaaggctc aggcggcgcg cttgaggggc gggtgaacgc cgcggcctgg   60
agtgggcggg gcctgacgcg ctctgccgct tccgcaggc gtgcatccgg gcctgcaagc   120
ccgacctctc cgccgagacg ccggtgttcc ccggcaacgg cgatgagcag ccgctgactg   180
agaacccccg gaagtacgtc atgggccatt tccgctggga ccgcttcggc cgtcggaatg   240
gtagcagcag cagcggagtt gggggcgcgg cccagaagcg cgaggaggaa gtggcggtgg   300
gcgaaggccc cgggccccgc ggcgatgacg ccgagacggg tccgcgcgag acaagcgtt   360 cttactccat ggaacacttc cgctgggca agccggtggg caagaagcgg cgcccggtga   420
aggtgtaccc caacggcgcc gaggacgagt cggcccagcc cttcccctc gaattcaaga   480 gggagctgac cggggagagg ctcgagcagg cgcgcggccc cgaggcccag gctgagagtg   540
cggccgcccg ggctgagctg gagtatggcc tggtggcgga ggcggaggct gaggcggccg   600
agaagaagga ctcggggccc tataagatgg aacacttccg ctggggcagc ccgcccaagg   660
acaagcgcta cggcgggttc atgacctccg agaagagcca aacgcccctt gtcacgctgt   720
tcaaaaacgc catcatcaag aacgcccaca agaagggcca gtgagggcgc agcgggcagg   780
ggcctctctc cgcggaaagt tgaccctgaa ggcctctctt ctgccctcct accgcctcgc   840
agcctgggtg aggattcgcc caggcagtga tggcgccagg tatcccgact cttaaagctg   900
tctgtagtta agaaataaaa cctttcaagt ttcacgaata ttgactgggt gaattaaaaa   960
cgcatttcca tcaagtaaag ggcagtacat attggagggg cg                    1002
```

```
<210> SEQ ID NO 3
<211> LENGTH: 1809
<212> TYPE: DNA
<213> ORGANISM: Bos taurus
<220> FEATURE:
<221> NAME/KEY: misc_feature
<222> LOCATION: (1069)...(1069)
<223> OTHER INFORMATION: SNP
<300> PUBLICATION INFORMATION:
<308> DATABASE ACCESSION NUMBER: GenBank AF265221
<309> DATABASE ENTRY DATE: 2001-11-09

<400> SEQUENCE: 3
cagcctaaga tttccaagtg atgctgacca gagccacact tgaaagagac tgaaaacttc   60
```

-continued

```
cttttccagct ccggagcatg ggacatttat tcacagcagg catgccactc tccgccgcct      120
aactttcgtt tggggcaagt caagactgga gaaaggtgct gaggctgcca gatccaggag      180
gttcagtcag tccagagggg acctgaatcc aaaatgaact ctacccagcc ccttgggatg      240
cacacctctc tccactcctg gaaccgcagc gcccacggaa tgcccaccaa tgtcagtgag      300
tccctggcaa aaggctactc ggacgggggg tgctatgagc agctctttgt ctctcccgag      360
gtgtttgtga ctctgggggt catcagcttg ttggagaata ttctggtgat cgtggccata      420
gccaagaaca agaatctgca ctcacccatg tactttttca tctgcagcct ggctgtggct      480
gacatgttgg tgagcgtttc caacgggtcg gaaaccattg tcatcaccct gctgaacagc      540
acggacacgg acgcgcagag cttcacggtg gatattgaca atgtcattga ctcggtgatc      600
tgtagctcct tgcttgcctc catctgcagc ttgctgtcga tcgcggtgga caggtacttc      660
actatcttct atgcgctcca gtaccataac atcatgacgg tgaagcgggt ggcgatcacc      720
atcagcgcca tctgggcagc ctgcacggtg tcgggcgtct tgttcatcat ttactcagac      780
agcagtgctg ttatcatctg cctcatcacc gtgttcttca ccatgctggc tctcatggcg      840
tctctctatg tccacatgtt cctcatggcc agactccaca ttaagaggat cgcggtcctg      900
ccaggtagcg gcaccatccg ccagggcgcc aacatgaagg gggcgattac cctgaccata      960
ctgatcgggg tctttgttgt ctgctgggcc cccttcttcc tgcacctgat attctacatc     1020
tcttgtcccc agaacccata ctgtgtgtgt ttcatgtctc actttaacct gtacctcatc     1080
ctcatcatgt gcaattccat cattgaccct ctgatttatg ccctgcggag ccaagaactg     1140
aggaaaacct tcaaagagat catttgttgc tctcctctag gtggcctctg tgatttgtct     1200
agcagatatt aaatggggac aaacgcgatg ctaaacacaa gcttaagaga ctttctcctt     1260
ctcatatgta caacctgaac agtctgtatc agccacagct ttttcttctg tgtagggcat     1320
ggagtgaaaa tttctattgt atcagttgaa gtttgtgatt tttttctgat gtgaaacagt     1380
gcccagtctt ggtgtatttt taatgtcatg ctactttctg gctgtaaaat gtgaatccac     1440
atcacaggtt ataggcacta tgcatttata aaaaagaag aaaaaaagtc cttatgagga     1500
gtttaacagt gtttccttct tgttatttac aaggatgtga cactttgctt gcttttgtaa     1560
catgaaaatc acagcttcat taagtatatc ctcataagtg gttttttat gttatacttt     1620 acaacactga agtgtaaaaa tttgattcta gcatttaggg gagaaatatt gagaacatat     1680
tgcttaatca taaaaacaa gctgaaattt caggtaattt aataagactt tctcattcat     1740
tcttcctgtg cagaagttga aatgaagctt gtattgggag aaaacagtt acttaaaaaa     1800 aaaaaaaaa                                                             1809
```

<210> SEQ ID NO 4
<211> LENGTH: 22
<212> TYPE: DNA
<213> ORGANISM: Bos taurus
<220> FEATURE:
<221> NAME/KEY: misc_feature
<222> LOCATION: (0)...(0)
<223> OTHER INFORMATION: Forward primer for DNA amplification of
      sequenceswithin SEQ ID NO: 1

<400> SEQUENCE: 4
gcgcccgcta aaatgcgact ga        22

<210> SEQ ID NO 5
<211> LENGTH: 20

```
<212> TYPE: DNA
<213> ORGANISM: Bos taurus
<220> FEATURE:
<221> NAME/KEY: misc_feature
<222> LOCATION: (0)...(0)
<223> OTHER INFORMATION: Reverse primer for DNA amplification;
      sequence is the reverse complement of the corresponding
      sequence in SEQ ID NO: 1

<400> SEQUENCE: 5
ctgtgatgcc tgccgggcac                                           20

<210> SEQ ID NO 6
<211> LENGTH: 21
<212> TYPE: DNA
<213> ORGANISM: Bos taurus
<220> FEATURE:
<221> NAME/KEY: misc_feature
<222> LOCATION: (0)...(0)
<223> OTHER INFORMATION: Forward primer for DNA amplification fo
      sequenceswithin SEQ ID NO: 2

<400> SEQUENCE: 6
cgtgcatccg ggcctgcaag c                                         21

<210> SEQ ID NO 7
<211> LENGTH: 23
<212> TYPE: DNA
<213> ORGANISM: Bos taurus
<220> FEATURE:
<221> NAME/KEY: misc_feature
<222> LOCATION: (0)...(0)
<223> OTHER INFORMATION: Reverse primer for DNA amplification;
      sequence is the reverse complement of the corresponding
      sequence in SEQ ID NO:2

<400> SEQUENCE: 7
gtcagctccc tcttgaattc gag                                       23

<210> SEQ ID NO 8
<211> LENGTH: 20
<212> TYPE: DNA
<213> ORGANISM: Bos taurus
<220> FEATURE:
<221> NAME/KEY: misc_feature
<222> LOCATION: (0)...(0)
<223> OTHER INFORMATION: Forward primer for DNA amplification of
      sequenceswithin SEQ ID NO: 3

<400> SEQUENCE: 8
taccctgacc atactgatcg                                           20

<210> SEQ ID NO 9
<211> LENGTH: 22
<212> TYPE: DNA
<213> ORGANISM: Bos taurus
<220> FEATURE:
<221> NAME/KEY: misc_feature
<222> LOCATION: (0)...(0)
<223> OTHER INFORMATION: Reverse primer for DNA amplification;
      sequence is the reverse complement of corresponding sequence
      in SEQ ID NO: 3

<400> SEQUENCE: 9
agagcaacaa atgatctctt tg                                        22
```